US00PP32744P3

(12) United States Plant Patent
Caster et al.

(10) Patent No.: US PP32,744 P3
(45) Date of Patent: Jan. 12, 2021

(54) BLUEBERRY PLANT VARIETY NAMED 'DRISBLUETWENTY'

(50) Latin Name: ***Vaccinium corymbosum* L.**
Varietal Denomination: DrisBlueTwenty

(71) Applicant: Driscoll's, Inc., Watsonville, CA (US)

(72) Inventors: Brian K. Caster, Watsonville, CA (US); Jennifer K. Izzo, Watsonville, CA (US); Bruce D. Mowrey, Watsonville, CA (US); Marta C. Baptista, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 16/501,199

(22) Filed: Mar. 5, 2019

(65) Prior Publication Data

US 2020/0288612 P1 Sep. 10, 2020

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 5/08
See application file for complete search history.

(56) References Cited

U.S. PATENT DOCUMENTS

PP6,699 P 3/1989 Wood
PP11,807 P2 3/2001 Lyrene
PP12,783 P2 7/2002 Lyrene
PP15,146 P3 9/2004 Hancock
PP20,436 P2 10/2009 Caster et al.
PP20,449 P2 11/2009 Caster et al.
PP20,488 P2 11/2009 Caster et al.
PP24,407 P3 4/2014 Caster et al.
PP24,489 P3 5/2014 Caster et al.
PP24,568 P3 6/2014 Caster et al.
PP24,569 P3 6/2014 Caster et al.
PP24,605 P3 7/2014 Caster et al.
PP26,287 P3 1/2016 Caster et al.
PP26,451 P3 3/2016 Caster et al.
PP26,537 P3 3/2016 Caster et al.
PP26,643 P3 4/2016 Caster et al.
PP26,748 P3 5/2016 Caster et al.
PP27,622 P3 1/2017 Caster et al.
PP28,933 P2 2/2018 Caster et al.

OTHER PUBLICATIONS

Caster et al., Unpublished U.S. Appl. No. 16/350,012, filed Sep. 12, 2018, titled "Blueberry Plant Variety Named 'DrisBlueEighteen'".
Caster et al., Unpublished U.S. Appl. No. 16/350,021, filed Sep. 13, 2018, titled "Blueberry Plant Variety Named 'DrisBlueSeventeen'".
Mowrey et al., Unpublished U.S. Appl. No. 16/350,020, filed Sep. 13, 2018, titled "Blueberry Plant Variety Named 'DrisBlueSixteen'".
Mowrey et al., Unpublished U.S. Appl. No. 16/350,226, filed Oct. 16, 2018, titled "Blueberry Plant Variety Named 'DrisBlueNineteen'".

*Primary Examiner* — Kent L Bell
(74) *Attorney, Agent, or Firm* — Morrison & Foerster LLP

(57) ABSTRACT

A new and distinct variety of blueberry plant named 'DrisBlueTwenty', particularly selected as a vigorous and upright highbush blueberry variety having a chilling requirement of at least 1000 hours of winter temperatures below 7° C., and with fruit ripening mid- to late season that are medium to large in size, firm, with a heavy persistent waxy bloom, is disclosed.

5 Drawing Sheets

Botanical classification: *Vaccinium corymbosum* L.

Varietal denomination: The varietal denomination of the claimed variety of blueberry plant is 'DrisBlueTwenty'.

BACKGROUND OF THE INVENTION

Blueberry plants are perennial flowering plants with indigo-colored berries from the section Cyanococcus within the genus *Vaccinium*. Many commercially sold species with English common names, including blueberry, are currently classified in section Cyanococcus of the genus *Vaccinium* and come predominantly from North America. Many North American native species of blueberries are grown commercially in the Southern Hemisphere in Australia, New Zealand, and South American nations.

*Vaccinium corymbosum*, the northern highbush blueberry, is a North American species of blueberry which has become a food crop of significant economic importance. It is native to eastern Canada and the eastern and southern United States, from Ontario east to Nova Scotia and south as far as Florida and eastern Texas. It has been naturalized in Europe, Japan, New Zealand, and the Pacific Northwest of North America. Other common names include blue huckleberry, tall huckleberry, swamp huckleberry, high blueberry, and swamp blueberry.

Blueberries are usually erect, prostrate shrubs that can vary in size from approximately four inches to approximately 13 feet in height. In the commercial production of blueberries, the smaller species are known as "lowbush blueberries", while the larger species are known as "highbush blueberries".

Blueberry bushes typically bear fruit in the middle of the growing season. However, fruiting times can be affected by local conditions such as altitude and latitude. As such, peak crop can vary from May to August in the northern hemisphere, depending upon these conditions.

Blueberries are a popular fruit that is typically consumed as fresh fruit, individually quick frozen (IQF) fruit, or in prepared foods, such as purées, juices, jellies, jams, baked goods, snack foods, and cereals.

Blueberry is an important and valuable fruit crop. Accordingly, there is a need for new varieties of blueberry plant. In particular, there is a need for improved varieties of blueberry plant that are stable, high yielding, and agronomically sound.

SUMMARY OF THE INVENTION

In order to meet these needs, the present invention is directed to an improved variety of blueberry plant. In particular, the invention relates to a new and distinct variety of blueberry plant (*Vaccinium corymbosum* L.), which has been denominated as 'DrisBlueTwenty'.

Blueberry plant variety 'DrisBlueTwenty' originated from a cross between the proprietary female parent blueberry plant 'G455' (unpatented) and the proprietary male parent blueberry plant 'MS122' (unpatented). Progeny plants from this cross, including 'DrisBlueTwenty', were asexually propagated via cuttings in Monterey County, Calif. in July of 2004. Blueberry plant variety 'DrisBlueTwenty' was later specifically identified and selected in Skagit County, Wash. in August of 2004.

'DrisBlueTwenty' was subsequently asexually propagated via cuttings and underwent further testing in Linn County, Oreg. for eight years (2011 to 2018). The present blueberry variety has been found to be stable and reproduce true to type through successive asexual propagations via cuttings.

'DrisBlueTwenty' exhibits the following distinguishing characteristics when grown under normal horticultural practices in Linn County, Oreg.:

1. Ovate leaf shape;
2. Round fruit shape in longitudinal section; and
3. Incurving type of fruit sepals.

'DrisBlueTwenty' was selected as a vigorous and upright highbush blueberry variety having a chilling requirement of at least 1000 hours of winter temperatures below 7° C., and with fruit ripening mid- to late season that are medium to large in size, firm, with a heavy persistent waxy bloom.

BRIEF DESCRIPTION OF THE DRAWINGS

This new blueberry plant variety is illustrated by the accompanying photographs. The colors shown are as true as can be reasonably obtained by conventional photographic procedures. The photographs are of plants that are seven years old.

DETAILED BOTANICAL DESCRIPTION

Figure 1:
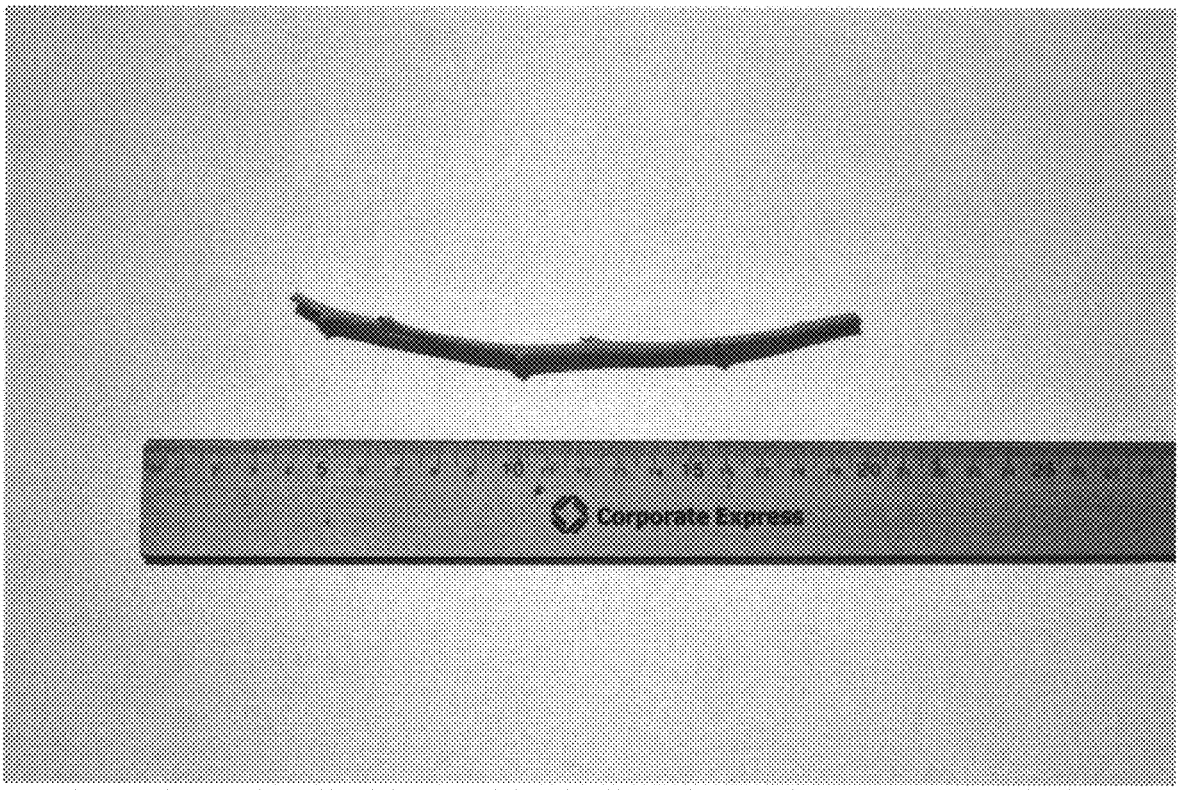
FIG. 1 illustrates a section of a cane of variety 'DrisBlueTwenty'.
Figure 2:
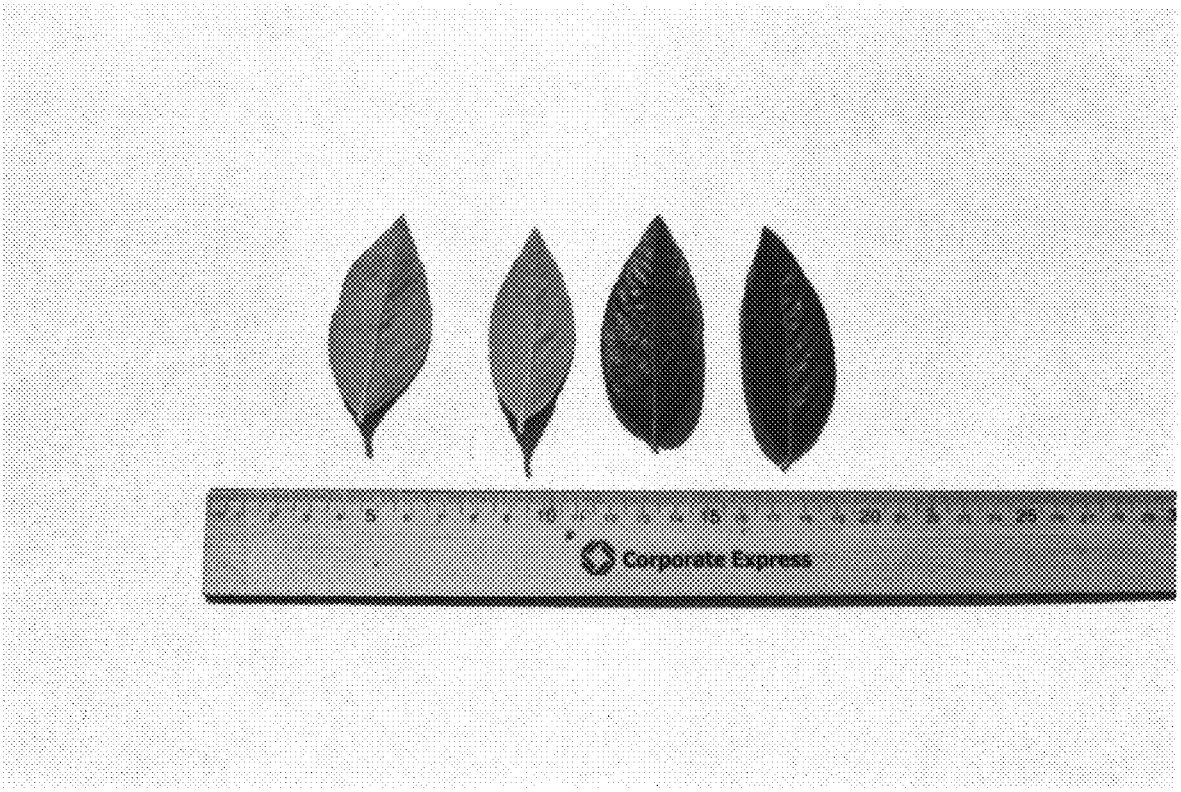
FIG. 2 illustrates leaves of variety 'DrisBlueTwenty'.
Figure 3:
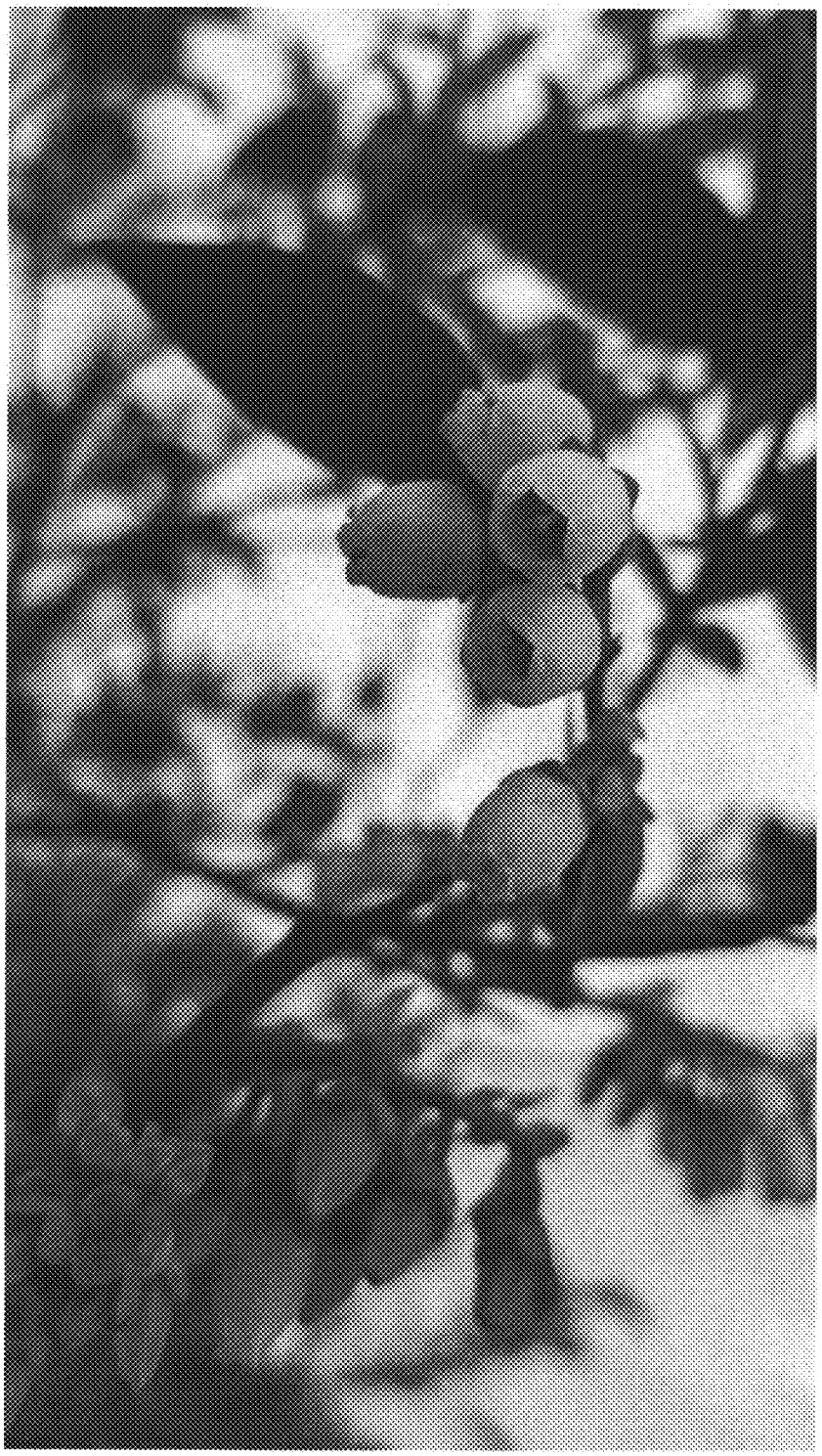
FIG. 3 illustrates flowers of variety 'DrisBlueTwenty'.
Figure 4:
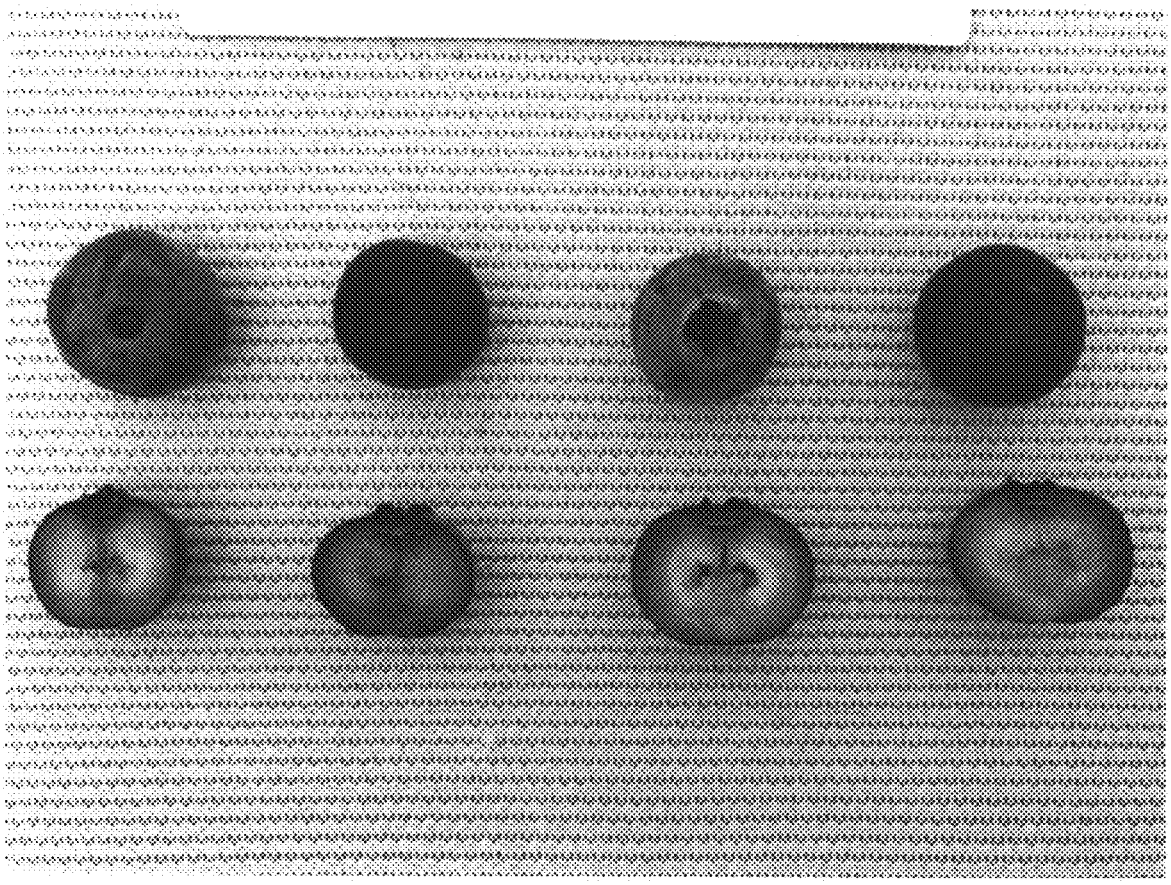
FIG. 4 illustrates whole fruit and cross-sections of the fruit of variety 'DrisBlueTwenty'.
Figure 5:
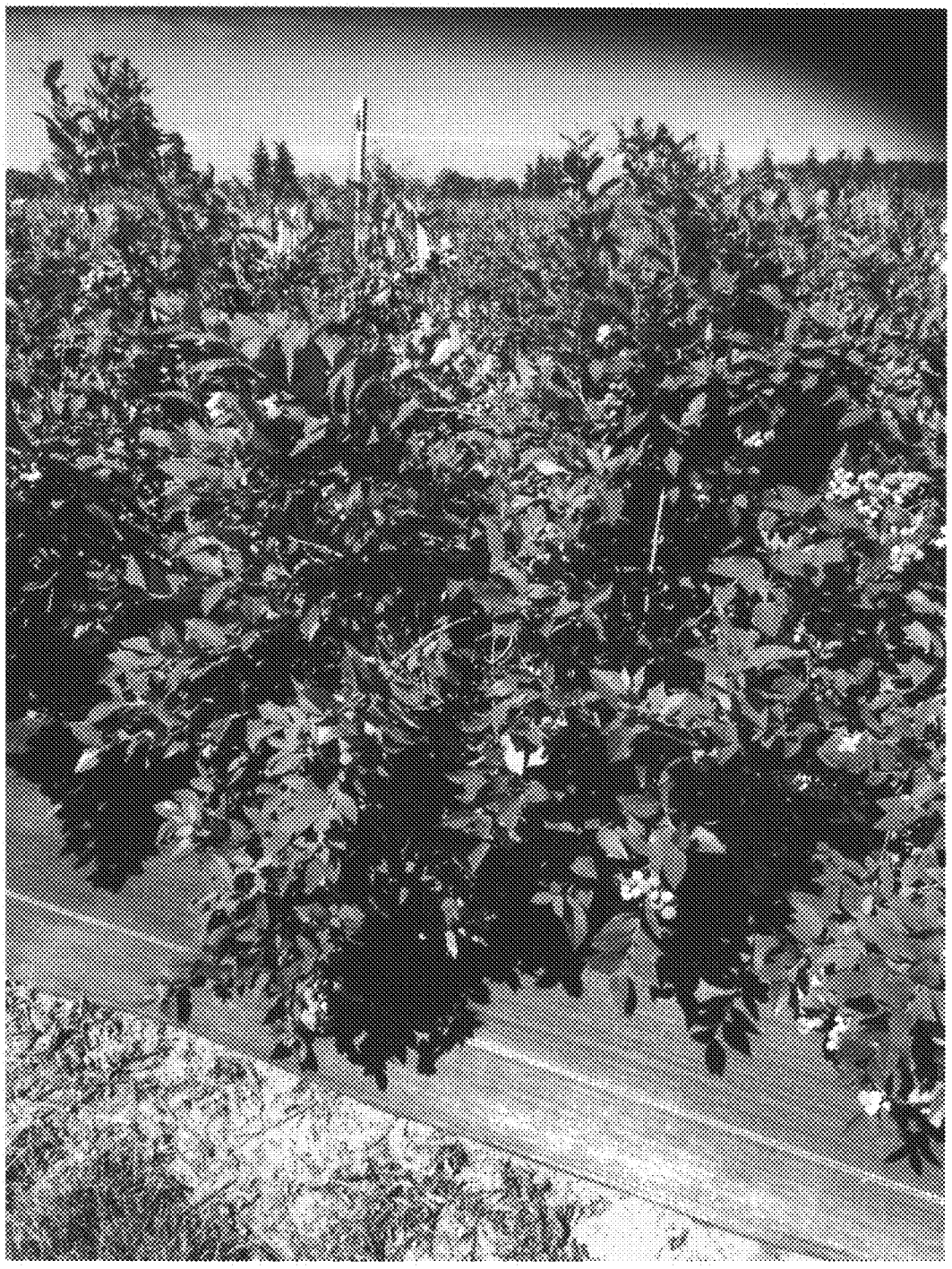
FIG. 5 illustrates plants of variety 'DrisBlueTwenty'.

The following description sets forth the distinctive characteristics of 'DrisBlueTwenty'. The data which define these characteristics is based on observations taken in Linn County, Oreg. from 2011 to 2018. This description is in accordance with UPOV terminology. Color designations, color descriptions, and other phenotypical descriptions may deviate from the stated values and descriptions depending upon variation in environmental, seasonal, climatic and cultural conditions. 'DrisBlueTwenty' has not been observed under all possible environmental conditions. The botanical description of 'DrisBlueTwenty' was taken from seven-year-old plants, unless noted otherwise. The indicated values represent averages calculated from measurements of several plants. Color references are primarily to The R.H.S. Colour Chart of The Royal Horticultural Society of London (R.H.S) (2007 edition). Descriptive terminology follows the *Plant Identification Terminology, An Illustrated Glossary,* $2^{nd}$ edition by James G. Harris and Melinda Woolf Harris, unless where otherwise defined.

Classification:

*Family*.—Ericaceae.

*Botanical*.—*Vaccinium corymbosum* L.

*Common name*.—Blueberry.

*Variety name*.—'DrisBlueTwenty'.

Parentage:

*Female parent*.—The proprietary blueberry plant 'G455' (unpatented).

*Male parent*.—The proprietary blueberry plant 'MS122' (unpatented).

Plant:

*Height*.—122.2 cm.

*Width*.—156.5 cm.

*Length/width ratio*.—0.8.

*Growth habit*.—Semi-upright.

*Chilling requirement*.—At least 1,000 hours of winter temperatures below 7° C. required for proper floral and vegetative budbreak.

*One-year-old canes* (*young canes*).—Length: 26 cm. Diameter at the base: 4 mm. Diameter at the tip: 3 mm. Internode length on the upper half: 16.3 mm. Color: RHS 167A (Moderate orange). One-year-old cane surface texture: Smooth.

*Five-year-old canes* (*mature canes*).—Length: 40 cm. Diameter at the base: 18 mm. Diameter at the tip: 14 mm. Five-year-old cane surface texture: Rough.

*Flower bud anthocyanin color*.—RHS N57B (Red-purple).

Leaves:

*Length*.—71.8 mm.

*Width*.—30.8 mm.

*Length/width ratio*.—2.3.

*Internode length*.—19.49 mm.

*Shape*.—Ovate.

*Margin*.—Entire.

*Color on upper side*.—RHS 137A (Green).

*Color of lower side*.—RHS N138C (Pale green).

*Shape of the leaf apex*.—Acute.

*Shape of the leaf base*.—Cuneate.

*Venation pattern of upper leaf surface*.—Reticulate.

*Venation pattern of lower leaf surface*.—Reticulate.

*Petiole*.—Length: 4.0 mm. Diameter: 1.49 mm. Petiole color: RHS 145A (Strong yellow-green).

Flowers:

*Length* (*excluding peduncle*).—10.83 mm.

*Diameter*.—6.71 mm.

*Length/width ratio*.—1.6.

*Flower bud* (*inflorescence bud*).—Length: 8.84 mm. Width: 4.15 mm. Number of flowers per bud: 8. Color of bud: RHS 138B (Moderate yellow-green).

*Flower pedicel.*—Length: 5.60 mm. Diameter: 1.27 mm. Pedicel color: RHS 145B (Light yellow-green).

*Corolla.*—Length of corolla: 11.1 mm. Width of corolla: 5.3 mm. Shape: Urceolate. Anthocyanin coloration of corolla tube: Present. Anthocyanin color of corolla tube: RHS 62D (Red-purple). Ridges on corolla tube: Present. Petal width (ridge to ridge): 2.05 mm. Petal length: 10 mm. Petal apex: Emarginate. Color of petal upper surface: RHS 155D (White). Color of petal lower surface: RHS 155D (White). Diameter of corolla aperture: 3.14 mm.

*Calyx.*—Diameter of calyx: 7.9 mm. Calyx upper surface color: RHS 139B (Moderate yellowish green). Calyx lower surface color: RHS 138A (Green).

*Sepal.*—Number of sepals per flower: 5. Sepal shape: Obtuse. Sepal length: 3.8 mm. Sepal width: 4.3 mm. Sepal apex: Obtuse. Sepal margin: Entire. Color of sepal upper surface: RHS 138A (Green). Color of sepal lower surface: RHS 138A (Green).

*Reproductive organs.*—Style length (including stigma): 8.71 mm.

*Flowering interval on one-year shoot.*—Mid-April to early June.

Fruit:

*Length.*—13.38 mm.

*Diameter.*—17.61 mm.

*Length/width ratio.*—0.8.

*Shape in longitudinal section.*—Round.

*Attitude of sepals.*—Erect to semi-erect.

*Type of sepals.*—Incurving.

*Calyx basin.*—Diameter: 5.96 mm. Depth: 2.11 mm. Diameter/depth ratio: 2.8.

*Weight.*—1.65 g.

*Firmness.*—Medium.

*Sweetness.*—Medium.

*Acidity.*—Medium.

*Number of berries per cluster.*—6.50.

*Peduncle length.*—23.29 mm.

*Peduncle color.*—RHS 138B (Moderate yellow-green).

*Diameter of fruit pedicel.*—1.24 mm.

*Seed.*—Length: 1.23 mm. Width: 0.73 mm. Length/width ratio: 1.7. Seed color: RHS 165A (Moderate brown).

*Color of unripe fruit.*—RHS 144A (Yellow-green).

*Color of fruit skin (after removal of bloom).*—RHS 103A (Blue).

*Color of fruit skin (with bloom).*—RHS 98D (Purplish blue).

*Berry flesh color.*—RHS 145C (Light yellow-green).

*Fruiting type.*—On one-year-old shoots.

*Ripening interval (harvest season) on one-year-old shoot.*—Mid-July to early September.

*Fruit storage quality.*—Following harvest, fruit have been stored for 21 days when maintained under cooled temperatures that are standard for blueberry storage.

*Productivity per plant per season.*—4 kg to 7 kg of fruit.

*Yield.*—15,000 kg to 25,000 kg of fruit per hectare per season from 72-month-old plants when grown at Albany, Oreg.

Resistance to abiotic stress, pests, and diseases:

*Heat.*—Moderately resistant.

*Cold hardiness.*—Plants have survived winter temperatures of −4° C.

*Spotted-wing drosophila (Drosophila suzukii).*—Moderately susceptible.

*Botrytis fruit rot (Botrytis cinerea).*—Moderately susceptible.

*Verticillium wilt (Verticillium spp.).*—Moderately resistant.

*Phomopsis cane dieback.*—Moderately susceptible.

COMPARISONS TO PARENTAL AND COMMERCIAL BLUEBERRY VARIETIES

'DrisBlueTwenty' differs from the proprietary female parent and commercial blueberry plant variety 'G455' (unpatented) in that fruit of 'DrisBlueTwenty' are larger in size, have a more persistent waxy bloom, and are sweeter-tasting compared to fruit of 'G455'.

'DrisBlueTwenty' differs from the proprietary male parent 'MS122' (unpatented) in that 'DrisBlueTwenty' has a much higher chilling requirement for proper reproductive and vegetative development and is more upright in growth habit when compared to 'MS122'.

'DrisBlueTwenty' differs from the commercial blueberry plant variety 'Liberty' (U.S. Plant Pat. No. 15,146) in that 'DrisBlueTwenty' has a semi-upright growth habit, whereas 'Liberty' has an upright to semi-upright growth habit. Moreover, leaves of 'DrisBlueTwenty' are ovate in shape with an entire leaf margin, whereas leaves of 'Liberty' are ovate to elliptic in shape with a serrate leaf margin. Further, flowers of 'DrisBlueTwenty' have strong anthocyanin coloration of corolla tube, whereas flowers of 'Liberty' have absent or very weak anthocyanin coloration of corolla tube. In addition, 'DrisBlueTwenty' is more vigorous, has higher yield, and produces fruit that are firmer in texture and sweeter-tasting when compared to 'Liberty'.

'DrisBlueTwenty' differs from the commercial blueberry plant variety 'DrisBlueFourteen' (U.S. Plant Pat. No. 27,622) in that leaves of 'DrisBlueTwenty' have a small length/width ratio and are ovate in shape, whereas leaves of 'DrisBlueFourteen' have a large length/width ratio and are elliptic in shape. Moreover, fruit of 'DrisBlueTwenty' have a round shape in longitudinal section with an incurving type of sepals, whereas fruit of 'DrisBlueFourteen' have an oblate shape in longitudinal section with a reflexed type of sepals. In addition, 'DrisBlueTwenty' is less susceptible to high temperature heat damage to leaves and fruit, is more vigorous growing, and has a more persistent waxy bloom on fruit when compared to 'DrisBlueFourteen'.

What is claimed is:

1. A new and distinct variety of blueberry plant designated 'DrisBlueTwenty' as shown and described herein.

* * * * *